US012237072B2

(12) United States Patent
Olson et al.

(10) Patent No.: US 12,237,072 B2
(45) Date of Patent: *Feb. 25, 2025

(54) DIGITIZATION OF AN OPERATING ROOM (71) Applicant: Verb Surgical Inc., Santa Clara, CA (US)

(72) Inventors: Blade A. Olson, Mountain View, CA (US); Bernhard A. Fuerst, Sunnyvale, CA (US); Alexander Barthel, Sunnyvale, CA (US); Yiming Xu, Foster City, CA (US); Giacomo Taylor, San Francisco, CA (US); Tianyu Song, Mountain View, CA (US)

(73) Assignee: Verb Surgical Inc., Santa Clara, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/449,270

(22) Filed: Aug. 14, 2023

(65) Prior Publication Data

US 2024/0038367 A1 Feb. 1, 2024

Related U.S. Application Data (63) Continuation of application No. 16/894,587, filed on Jun. 5, 2020, now Pat. No. 11,756,672.

(51) Int. Cl.
*A61B 17/00* (2006.01)
*A61B 1/00* (2006.01)
(Continued)

(52) U.S. Cl.
CPC ......... *G16H 30/20* (2018.01); *A61B 1/00009* (2013.01); *A61B 34/20* (2016.02);
(Continued)

(58) Field of Classification Search
CPC ........ G16H 30/20; G16H 40/20; G16H 40/63; G16H 50/20; G16H 30/40; G16H 40/60;
(Continued)

(56) References Cited

U.S. PATENT DOCUMENTS 10,096,122 B1 * 10/2018 Agrawal ................... G06T 7/90
2015/0331425 A1    11/2015 Chen et al.
(Continued)

OTHER PUBLICATIONS

International Search Report and Written Opinion for International Application No. PCT/US2020/037923 mailed Feb. 25, 2021, 17 pages.

(Continued)

*Primary Examiner* — Xin Jia
(74) *Attorney, Agent, or Firm* — Aikin & Gallant, LLP (57) ABSTRACT A surgical exercise performed with a surgical robotic system is sensed by depth cameras, generating 3D point cloud data. Robot system data associated with the surgical robotic system is logged. Object recognition is performed on image data produced by the one or more depth cameras, to recognized objects, including surgical equipment and people, in the operating room (OR). The surgical exercise is digitized by storing the 3D point cloud data of unrecognized objects, a position and orientation associated with the recognized objects, and c) the robot system data.

20 Claims, 6 Drawing Sheets (51) Int. Cl.

| | | |
|---|---|---|
| *A61B 34/20* | (2016.01) | |
| *A61B 34/37* | (2016.01) | |
| *G06F 16/901* | (2019.01) | |
| *G06T 7/00* | (2017.01) | |
| *G06T 7/50* | (2017.01) | |
| *G06T 7/70* | (2017.01) | |
| *G06T 17/20* | (2006.01) | |
| *G06V 20/10* | (2022.01) | |
| *G16H 30/20* | (2018.01) | |
| *G16H 40/20* | (2018.01) | |
| *G16H 40/63* | (2018.01) | |
| *G16H 50/20* | (2018.01) | |
| *A61B 17/34* | (2006.01) | |

(52) U.S. Cl.
CPC .......... *A61B 34/37* (2016.02); *G06F 16/9024* (2019.01); *G06T 7/0012* (2013.01); *G06T 7/50* (2017.01); *G06T 7/70* (2017.01); *G06T 17/20* (2013.01); *G06V 20/10* (2022.01); *G16H 40/20* (2018.01); *G16H 40/63* (2018.01); *G16H 50/20* (2018.01); *A61B 17/3423* (2013.01); *A61B 2034/2057* (2016.02); *G06T 2207/10024* (2013.01); *G06T 2207/10028* (2013.01); *G06T 2207/30004* (2013.01)

(58) Field of Classification Search
CPC ................ G16H 30/00; A61B 1/00009; A61B 34/20; A61B 34/37; A61B 17/3423; A61B 2034/2057; A61B 2034/2065; A61B 2090/371; A61B 34/30; A61B 90/361; G06F 16/9024; G06T 7/0012; G06T 7/50; G06T 7/70; G06T 17/20; G06T 2207/10024; G06T 2207/10028; G06T 2207/30004; G06V 20/10; G01B 11/245
See application file for complete search history.

(56) References Cited

U.S. PATENT DOCUMENTS

| | | |
|---|---|---|
| 2018/0275632 A1 | 9/2018 | Zhang et al. |
| 2019/0038362 A1* | 2/2019 | Nash ................ H04N 13/239 |
| 2020/0110936 A1 | 4/2020 | Hares et al. |
| 2020/0138534 A1 | 5/2020 | Garcia Kilroy et al. |
| 2020/0375666 A1* | 12/2020 | Murphy ................ A61B 34/20 |

OTHER PUBLICATIONS

International Preliminary Report on Patentability for International Application No. PCT/US2020/037923 mailed Dec. 15, 2022, 11 pages.

* cited by examiner

PLAYBACK OF PROCEDURE

EVENT/ACCESSIBLE POINT 70

DIGITIZATION OF AN OPERATING ROOM

CROSS-REFERENCE TO RELATED APPLICATION

This application is a continuation application of co-pending U.S. patent application Ser. No. 16/894,587, filed on Jun. 5, 2020, which is incorporated by reference herein.

TECHNICAL FIELD

This invention relates generally to surgical robotic systems, and more specifically to digitizing a surgical exercise that is performed with a surgical robotic system.

BACKGROUND

Minimally-invasive surgery (MIS), such as laparoscopic surgery, involves techniques intended to reduce tissue damage during a surgical procedure. For example, laparoscopic procedures typically involve creating a number of small incisions in the patient (e.g., in the abdomen), and introducing one or more tools and at least one camera through the incisions into the patient. The surgical procedures can then be performed by using the introduced surgical tools, with the visualization aid provided by the camera.

Generally, MIS provides multiple benefits, such as reduced patient scarring, less patient pain, shorter patient recovery periods, and lower medical treatment costs associated with patient recovery. MIS can be performed with surgical robotic systems that include one or more robotic arms for manipulating surgical tools based on commands from a remote operator. A surgical robotic arm may, for example, support at its distal end various devices such as surgical end effectors, imaging devices, cannulas for providing access to the patient's body cavity and organs, etc. Control of such robotic systems may require control inputs from a user (e.g., surgeon or other operator) via one or more user interface devices that translate manipulations or commands from the user into control of the robotic system. For example, in response to user commands, a tool driver having one or more motors may actuate one or more degrees of freedom of a surgical tool when the surgical tool is positioned at the surgical site in the patient. Thus, a surgical robotic arm can assist in performing surgery.

Performance of surgery with surgical robotic systems can benefit from pre-operative planning, post-operative analysis, and intra-operative guidance. A system that captures image data can allow users to review and interact with a memorialization of a surgical exercise. Captured data can be used for pre-operative planning, post-operative analysis, and intra-operative guidance.

SUMMARY

In order to create uniformity within the surgical world, and to define an objective standard of surgery for novice surgeons to follow, extensive data collection can be undertaken in order to find commonalities between surgeons that have been trained from different universities, residencies, hospitals, and countries. Regardless of whether these commonalities are eventually derived from machine intelligence, or individual inspection and human intelligence, both approaches share a common problem: the need to digitize surgeries such that they can be replayed and analyzed quantitatively using off-line analysis.

Further, the digitization of the operating room should ideally eliminate storage of raw sensor data, as each surgery would create terabytes of information that would be difficult for humans and computers to store, replay, and review. The present disclosure describes digitization of an OR and surgical exercises that supports surgical replay, offline analysis, and intraoperative guidance in a manner that can support wide-scale deployment of a surgical robotic system to hospitals operating under different circumstances in different countries.

The present disclosure describes processes for reconstructing key temporal and spatial aspects of a surgical exercise such that it can be digitally reconstructed for pre-operative replay and planning, post-operative analysis, and intra-operative intervention. Depth cameras (e.g., RGBD sensors) can be integrated with a surgical robotic system (e.g., with a control tower) and on an untethered portable electronic device (e.g., a handheld computer tablet) to create a stream of point cloud data that is fused together. For example, one or more processors fuse this continuous RGBD point cloud stream with logged robot data from the surgical robotic system to create a common coordinate frame shared between an augmented reality tablet, the control tower, and the surgical table.

Point cloud data for a multi-hour surgery can be too large to be stored in the cloud for every surgery, so semantic segmentation can be used to store only the sections of point cloud data that are not associated with a pre-defined, or classified, object that is recognized in the scene. This collection of classified, recognized objects and unclassified point cloud data are stored in the cloud for offline analysis.

Additionally, online analysis of recognizable objects in the scene, which are recognized by trained semantic segmentation machine learning models, can be used to alert operating room staff of important events intra-operatively. Altogether, the OR digitization processes described herein provide operating room staff with the ability to view replays of past surgeries, receive post-operative analysis of surgeries that have been analyzed either by artificial or human intelligence, and receive intraoperative alerts about key surgical events.

In some embodiments, a method is described for generating a digital asset that includes a recording of a surgical exercise, fused from 3D point cloud data and logged robotic system data. The surgical exercise is performed with a surgical robotic system. Performance of the surgical exercise, which could be a real surgical procedure, or a demonstration, is sensed by one or more depth cameras, also known as 3D scanners. Meanwhile, robot system data that is associated with the surgical robotic system is logged. The robot system data can include position, orientation and movement of robot arms, as well as other noteworthy indicators related to the system or the procedure.

Using computer vision, some objects can be recognized in image data produce by the depth cameras. Some objects, however, might not be recognized. The recognized objects can be memorialized by storing position and orientation of those objects as sensed in their environment. Thus, their memory footprint can be reduced. For unrecognized objects, image data such as 3D point cloud data or mesh data can be stored. The robot system data is also stored. The stored data can be saved as a digital asset and synchronized in time (e.g., with time stamps) and/or organized in one or more sequences of frames. The stored data can be used to reconstruct the surgical exercise for playback, provide real-time alerts during an operation, and used for offline analysis.

A playback device can reconstruct the surgical exercise using by rendering the recognized objects at the position and orientation specified in the digital asset. The stored image data (e.g., 3D point cloud or mesh) can be rendered with the recognized objects, sharing a common 3D coordinate system, and temporally synchronized. The stored robot system data can be used to reconstruct precise position, orientation and movement of the surgical robot (e.g., the robot arms and surgical tool) rendered for playback or for real-time analysis.

Events used as 'jump points' can be generated based on human activity and/or the robot system data, for noteworthy surgical events. For example, human activity and/or robot system data might indicate when, in the data, the UIDs are engaged for surgery, or when there is a surgeon change or an instrument change, when trocars are inserted, and more. A user can select an event during playback to jump to a relevant portion of the surgical exercise. Additional aspects and features are described in the present disclosure. The events can be generated through automated analysis of one or more of the data streams, and/or through analysis by people.

DETAILED DESCRIPTION

Examples of various aspects and variations of the invention are described herein and illustrated in the accompanying drawings. The following description is not intended to limit the invention to these embodiments, but rather to enable a person skilled in the art to make and use this invention.

The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosures.

Reference in the specification to "one embodiment" or "an embodiment" means that a particular feature, structure, or characteristic described in conjunction with the embodiment can be included in at least one embodiment of the disclosure. The appearances of the phrase "in one embodiment" in various places in the specification do not necessarily all refer to the same embodiment.

Figure 1:
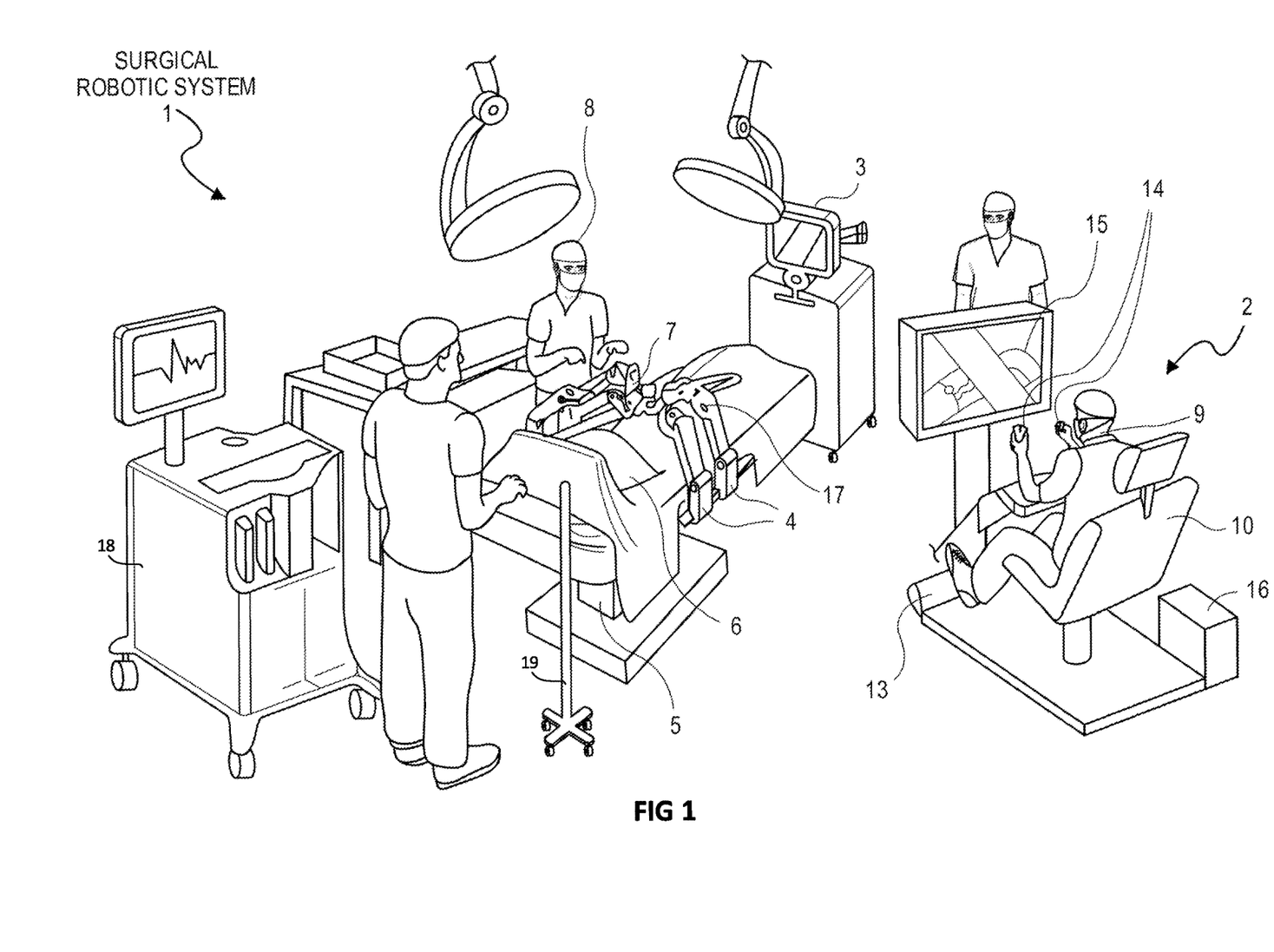
FIG. 1 illustrates a surgical robotic system according to one embodiment.

Referring to FIG. 1, this is a pictorial view of an example surgical robotic system 1 in an operating arena. The robotic system 1 includes a user console 2, a control tower 3, and one or more surgical robotic arms 4 at a surgical robotic platform 5, e.g., a table, a bed, etc. The system 1 can incorporate any number of devices, tools, or accessories used to perform surgery on a patient 6. For example, the system 1 may include one or more surgical tools 7 used to perform surgery. A surgical tool 7 may be an end effector that is attached to a distal end of a surgical arm 4, for executing a surgical procedure.

Each surgical tool 7 may be manipulated manually, robotically, or both, during the surgery. For example, the surgical tool 7 may be a tool used to enter, view, or manipulate an internal anatomy of the patient 6. In an embodiment, the surgical tool 7 is a grasper that can grasp tissue of the patient. The surgical tool 7 may be controlled manually, by a bedside operator 8; or it may be controlled robotically, via actuated movement of the surgical robotic arm 4 to which it is attached. The robotic arms 4 are shown as a table-mounted system, but in other configurations the arms 4 may be mounted in a cart, ceiling or sidewall, or in another suitable structural support.

Generally, a remote operator 9, such as a surgeon or other operator, may use the user console 2 to remotely manipulate the arms 4 and/or the attached surgical tools 7, e.g., teleoperation. The user console 2 may be located in the same operating room as the rest of the system 1, as shown in FIG. 1. In other environments however, the user console 2 may be located in an adjacent or nearby room, or it may be at a remote location, e.g., in a different building, city, or country. The user console 2 may comprise a seat 10, foot-operated controls 13, one or more handheld user input devices, UID 14, and at least one user display 15 that is configured to display, for example, a view of the surgical site inside the patient 6. In the example user console 2, the remote operator 9 is sitting in the seat 10 and viewing the user display 15 while manipulating a foot-operated control 13 and a handheld UID 14 in order to remotely control the arms 4 and the surgical tools 7 (that are mounted on the distal ends of the arms 4).

In some variations, the bedside operator 8 may also operate the system 1 in an "over the bed" mode, in which the beside operator 8 (user) is now at a side of the patient 6 and is simultaneously manipulating a robotically-driven tool (end effector as attached to the arm 4), e.g., with a handheld UID 14 held in one hand, and a manual laparoscopic tool. For example, the bedside operator's left hand may be manipulating the handheld UID to control a robotic component, while the bedside operator's right hand may be manipulating a manual laparoscopic tool. Thus, in these variations, the bedside operator 8 may perform both robotic-assisted minimally invasive surgery and manual laparoscopic surgery on the patient 6.

During an example procedure (surgery), the patient 6 is prepped and draped in a sterile fashion to achieve anesthesia. Initial access to the surgical site may be performed manually while the arms of the robotic system 1 are in a stowed configuration or withdrawn configuration (to facilitate access to the surgical site). Once access is completed, initial positioning or preparation of the robotic system 1 including its arms 4 may be performed. Next, the surgery proceeds with the remote operator 9 at the user console 2 utilizing the foot-operated controls 13 and the UIDs 14 to manipulate the various end effectors and perhaps an imaging system, to perform the surgery. Manual assistance may also be provided at the procedure bed or table, by sterile-gowned bedside personnel, e.g., the bedside operator 8 who may perform tasks such as retracting tissues, performing manual repositioning, and tool exchange upon one or more of the robotic arms 4. Non-sterile personnel may also be present to assist the remote operator 9 at the user console 2. When the procedure or surgery is completed, the system 1 and the user console 2 may be configured or set in a state to facilitate post-operative procedures such as cleaning or sterilization and healthcare record entry or printout via the user console 2.

In one embodiment, the remote operator 9 holds and moves the UID 14 to provide an input command to move a robot arm actuator 17 in the robotic system 1. The UID 14 may be communicatively coupled to the rest of the robotic system 1, e.g., via a console computer system 16. The UID 14 can generate spatial state signals corresponding to movement of the UID 14, e.g., position and orientation of the handheld housing of the UID, and the spatial state signals may be input signals to control a motion of the robot arm actuator 17. The robotic system 1 may use control signals derived from the spatial state signals, to control proportional motion of the actuator 17. In one embodiment, a console processor of the console computer system 16 receives the spatial state signals and generates the corresponding control signals. Based on these control signals, which control how the actuator 17 is energized to move a segment or link of the arm 4, the movement of a corresponding surgical tool that is attached to the arm may mimic the movement of the UID 14. Similarly, interaction between the remote operator 9 and the UID 14 can generate for example a grip control signal that causes a jaw of a grasper of the surgical tool 7 to close and grip the tissue of patient 6.

The surgical robotic system 1 may include several UIDs 14, where respective control signals are generated for each UID that control the actuators and the surgical tool (end effector) of a respective arm 4. For example, the remote operator 9 may move a first UID 14 to control the motion of an actuator 17 that is in a left robotic arm, where the actuator responds by moving linkages, gears, etc., in that arm 4. Similarly, movement of a second UID 14 by the remote operator 9 controls the motion of another actuator 17, which in turn moves other linkages, gears, etc., of the robotic system 1. The robotic system 1 may include a right arm 4 that is secured to the bed or table to the right side of the patient, and a left arm 4 that is at the left side of the patient. An actuator 17 may include one or more motors that are controlled so that they drive the rotation of a joint of the arm 4, to for example change, relative to the patient, an orientation of an endoscope or a grasper of the surgical tool 7 that is attached to that arm. Motion of several actuators 17 in the same arm 4 can be controlled by the spatial state signals generated from a particular UID 14. The UIDs 14 can also control motion of respective surgical tool graspers. For example, each UID 14 can generate a respective grip signal to control motion of an actuator, e.g., a linear actuator, that opens or closes jaws of the grasper at a distal end of surgical tool 7 to grip tissue within patient 6.

In some embodiments, the communication between the platform 5 and the user console 2 may be through a control tower 3, which may translate user commands that are received from the user console 2 (and more particularly from the console computer system 16) into robotic control commands that transmitted to the arms 4 on the robotic platform 5. The control tower 3 may also transmit status and feedback from the platform 5 back to the user console 2. The communication connections between the robotic platform 5, the user console 2, and the control tower 3 may be via wired and/or wireless links, using any suitable ones of a variety of data communication protocols. Any wired connections may be optionally built into the floor and/or walls or ceiling of the operating room. The robotic system 1 may provide video output to one or more displays, including displays within the operating room as well as remote displays that are accessible via the Internet or other networks. The video output or feed may also be encrypted to ensure privacy and all or portions of the video output may be saved to a server or electronic healthcare record system.

A surgical robotic arm can have movable, jointed, and/or motorized members with multiple degrees of freedom that can hold various tools or appendages at distal ends. Example systems include the da Vinci® Surgical System which can be used for minimally invasive surgery (e.g., urologic surgical procedures, general laparoscopic surgical procedures, gynecologic laparoscopic surgical procedures, general non-cardiovascular thoracoscopic surgical procedures and thoracoscopically assisted cardiotomy procedures). A "virtual surgical robotic arm" can be a computer generated model of a robotic arm rendered over the captured video of a user setup. The virtual surgical robotic arm can be a complex 3D model of the real robotic arm. Alternatively, or additionally, a virtual surgical robotic arm can include visual aids such as arrows, tool tips, or other representation relating to providing pose information about a robotic arm such as a geometrically simplified version of the real robotic arm.

Figure 2:
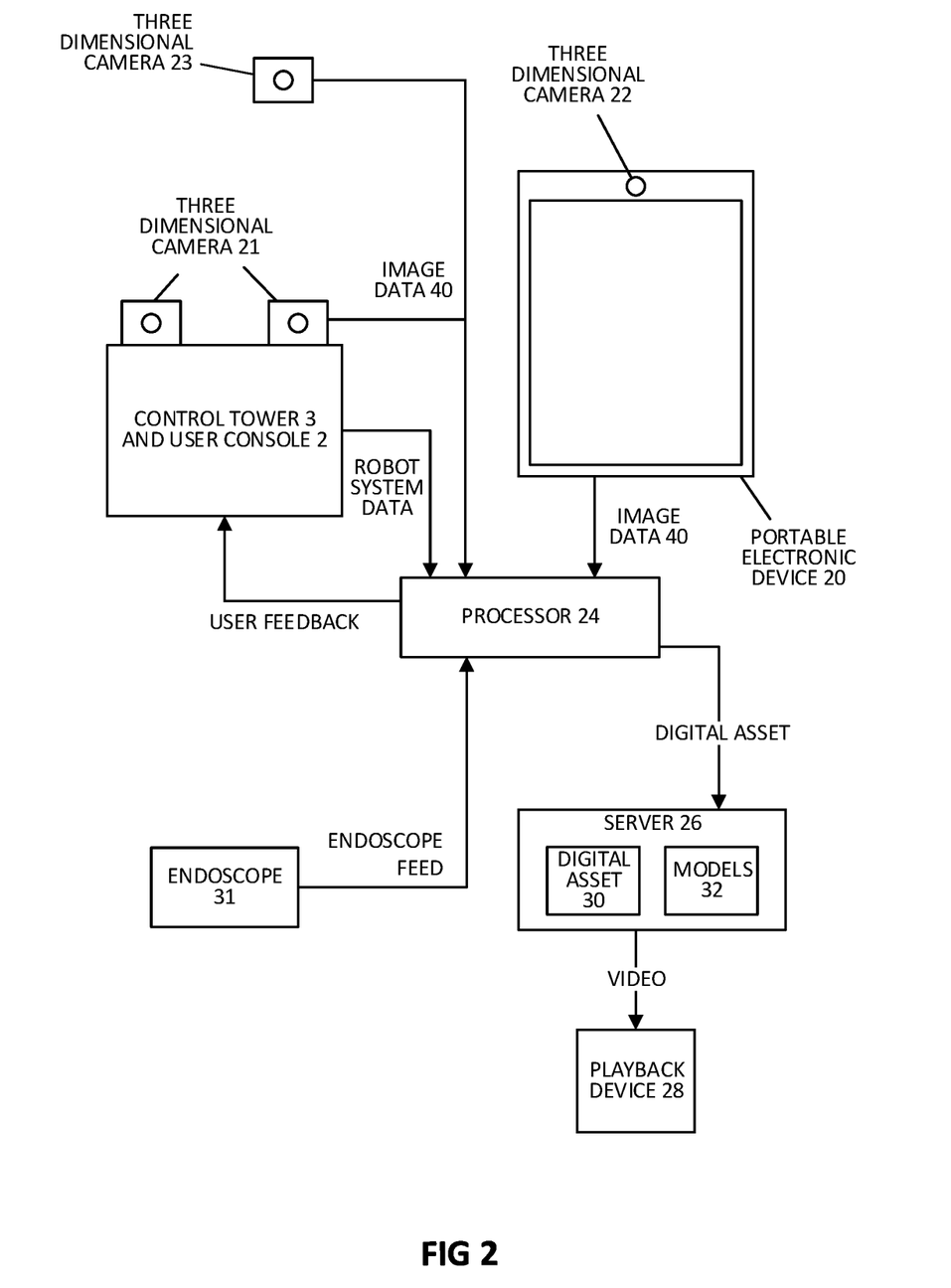
FIG. 2 and FIG. 3 show a system for capturing a surgical exercise, according to some embodiments.

A system for digitizing a surgical exercise is shown in FIG. 2 that includes one or more depth cameras (e.g., 3D scanning sensors 21, 22, and 23). These depth cameras can be arranged on or integrated with any of the surgical robotic system described in FIG. 1, for example, the control tower 3, the surgical table 5, and/or user console 2. Further, the depth cameras can be integrated with a portable electronic device 20, and/or mounted on a stand, walls, or a ceiling of an operating room. The depth cameras sense a surgical exercise performed with a surgical robotic system. The surgical exercise can be a real procedure performed on a real patient, a demonstration on a real patient or dummy, or other training exercise, using a surgical robotic system like that shown in FIG. 1.

In some embodiments, the system includes three to five depth cameras. The depth cameras can generate synchronized RGBD (color and depth) frames. These RGBD frames can be fused to make a singular sequence of wide-angle RGBD frames of the OR. The frame rate of the sensors can be changed dynamically by the system depending on which camera is deemed most important for retrieving data at any one point in time. The camera deemed most important can have an increased frame rate.

The portable electronic device 20 can be a computer tablet operated during the exercise by surgical staff that houses a 3D scanning sensor retrieving RGBD (color+depth) frames. These RGBD frames captured by the portable electronic device can be localized within 3D space by a continuously running SLAM (Simultaneous Localization and Mapping) algorithm that specifies where the tablet exists in 3D space relative to the surgical robotic system. The tablet communicates this image data (the RGBD frames) to the processor 24, which can be at various transfer rates depending on the speed of the Wi-Fi connection or other communication protocol in the OR.

During the procedure, robot system data that is associated with the surgical robotic system is logged. The logging can be concurrent with and synchronized with the image data captured by the depth cameras. The stream of robot system data can include user controls from the user console such as, for example, input state, position, or rotation of a user interface device (such as UID 14 in FIG. 1), or a state of a foot pedal (such as foot pedal 13), that are used to operate the surgical robotic system. The robot system data can also include real-time information describing state, position or rotation of a surgical instrument attached to a robot arm such as whether a grasper or cutter is open or closed or how far it is extended into a surgical workspace, or a force or energy applied with the surgical instrument. Further, movement, position and orientation of robot arms or the surgical table can be logged, such as joint values (describing a joint position) or mode (draped, undraped) of each of the robot arms. Other information such as network connectivity of the surgical robotic system, user log-in data, a graphical user interface state (e.g., what screen is active on a user display 15 shown in FIG. 1), and state of touchpoints on the surgical robotic system can also be included. The robot system data can be continuously logged, timestamped, and stored long-term in synchronization with the timestamped point cloud data.

The processor 24 can coordinate the robot system data with the image data 40 based on alignment of the time-stamps. The image data can be a collection of RGBD frames such that the combined data (a digital asset 30) can be reconstructed as a 3D mesh of the surgical robotic system (including the surgical robot, the control tower, the user console described in FIG. 1), and any pre-classified objects in the operating room, such as mayo stands, walls, floor, stools, shelves, lighting booms, and screens/monitors.

In some embodiments, an endoscope 31 can generate an endoscope feed that is also received by the processor and fused with the digitized surgical exercise. The endoscope feed can also be associated with and synchronized with the robot system data and image data for playback. The processor can compress the image data, the robot system data, and optionally, the endoscope feed, to a digital asset 30 which can be used for playback. The digital asset can be stored in an electronic device such as a network connected server 26. A playback device 28 can retrieve the digital asset for playback. As described in other sections, the processor can format the digital asset so that position and orientation of recognized objects are stored rather than raw image data or point cloud data.

For recognized objects, position and orientation can be determined with a common coordinate system as the unrecognized objects, walls, ceilings, and floors of the surgical robotic system. The playback device can access models 32 of the recognized objects to render them into a corresponding position and orientation with the unrecognized objects to render the OR and surgical exercise during playback (e.g., to a display).

In addition to synchronizing and compressing data of the surgical exercise for playback, the system can generate user feedback during the surgical exercise based on the robot system data or the position and orientation of the recognized objects. The user feedback can indicate at least one of: the user interface device is engaged for surgery, a change in surgeon, a change in instrument, docking of a trocar, insertion of trocar, phase change, slow performance of surgery, improper trocar position, improper patient position, arm collision, and improper OR staff position.

Such feedback can be generated automatically based on analysis of the data using machine learning algorithm and/or computer implemented logic. For example, based on position and movement of the surgical instrument and robot arms, endoscope feed, or other data, the processor can determine that a trocar is being inserted, angle of insertion, and whether or not this insertion is proper. In another example, based on computer vision, the processor can determine whether a patient is improperly positioned on a surgical table.

In another example, based on evaluation of the telemetry of the robotic system data, and comparison to known benchmarks or prior surgical exercises, the processor can determine that a surgical exercise is being performed too slow or too quick. If it is determined that a portion of the surgical procedure that involves cutting or removing of an organ is being performed faster or slower than an average or predetermined time by more than a threshold time amount, the system can provide feedback to the surgeon and staff, so that the can adjust the surgical exercise if appropriate.

In yet another example, the processor can analyze positions of surgical staff in the OR and determine whether they are correctly positioned, for example, a staff member might be standing at a foot of a patient. The processor can recognize the staff member and her position in the OR relative to the surgical table, and, based on reference to known benchmarks or predetermined parameters, determine that the staff member is not standing at a proper location. Feedback can be provided in real-time to alert the staff member to move towards the mid-section of the patient along the surgical table. All feedback can be given in real-time, e.g., with minimal delay (including unavoidable delays like those caused by processing, communication latency, and buffering of the data) to provide real-time feedback during a surgical procedure.

Figure 3:
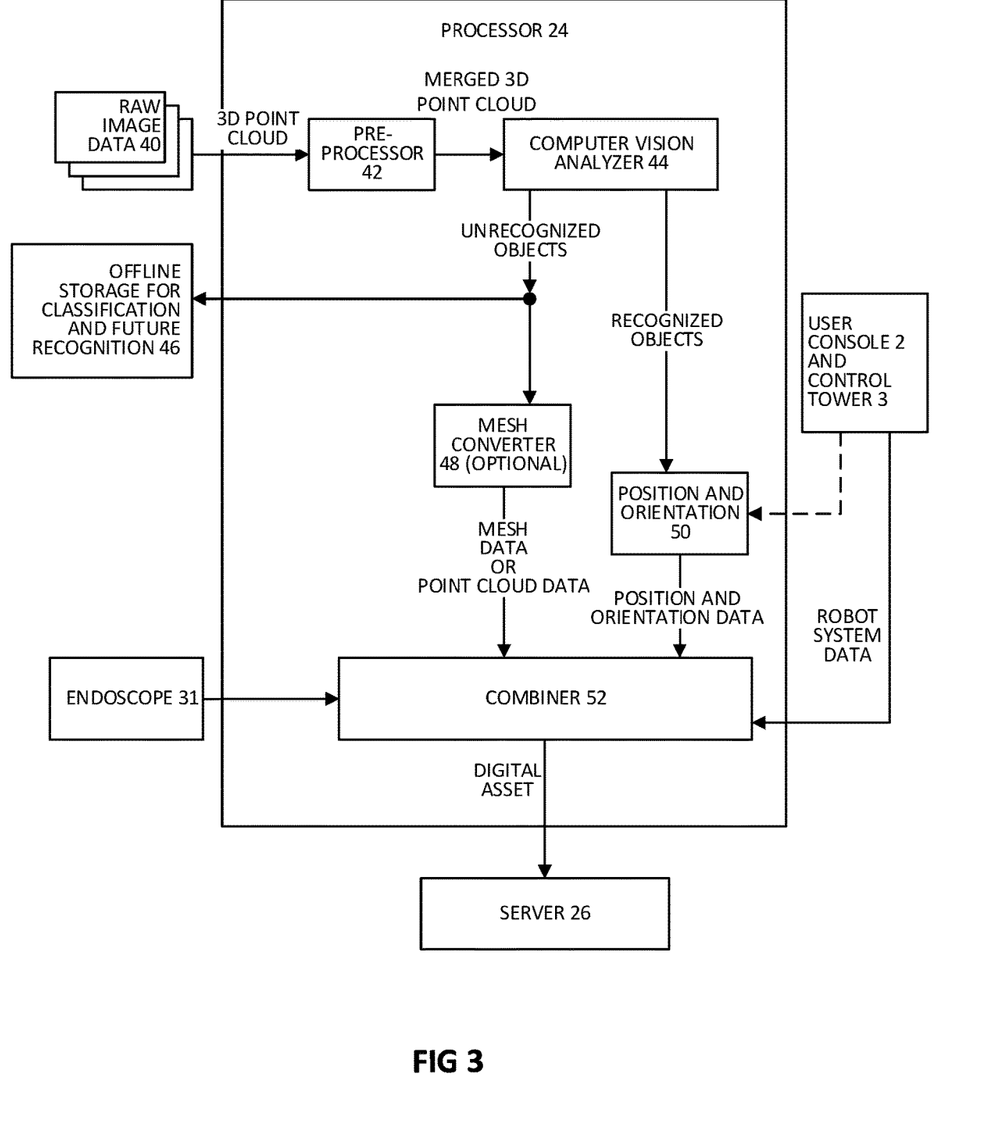

FIG. 3 shows processing of surgical exercise to form a digital asset 30 according to some embodiments. Raw image data describing, which can be 3D point cloud data, is received for processing. Point cloud data is a set of data points in space that are produced by 3D image capture devices. Point cloud data represent measurements of many points on external surfaces of objects sensed by the 3D image capture devices.

As raw image data 40 is collected (e.g., from cameras 21-23 in FIG. 2), the data can be processed at pre-processor block 42 before analysis. Here, point cloud data across frames can be de-noised, down sampled, and merged so that the density of the 3D point cloud is consistent in 3D space. A probability-based processing filter can be applied to determine which points should be maintained through time and which should be dropped, as objects in the scene are not guaranteed to be static.

As this common 3D point cloud is continuously updated, another process (which can be slower and operate in parallel with preprocessor) is performed at blocks 44, 48, and 50 to analyzed the updated points. Stable sections of points in the point cloud can be segmented from unstable sections to accelerate point cloud analysis. At mesh converter block 48, which is optional, background process can generate a 3D mesh of the point cloud with a reduced set of points representing vertices of a 3D polygonal shape. In regions (e.g., pixels) that the point cloud appears to include a known object, such as the surgical table and robot arms, the user console, a control tower, or other known and classified objects, the simplified 3D mesh of the point cloud is not calculated. Instead, a component transform describing a position and orientation of the recognized object in space takes the place of the recognized object. The position and orientation is aligned with the raw point cloud. It should be understood that orientation describes a direction or rotation of an object in the common 3D coordinate system.

In some embodiments, sections of the point cloud with significant updates will be processed to update the 3D mesh of those sections, while those without updates or below a threshold amount of change will not be updated. The 3D mesh of sections of the point cloud with unrecognized objects can be maintained (updated at sufficient rate) for consumer-facing features, such as, for example, in the case of a robot arm pathing around the patient's body, and in the case of determining a trocar placement on the patient given the size of the patient and the procedure.

To recognize objects, at block 44, computer vision analyzer 44 can detect and recognize, in the raw image data, objects such as, but not limited to, the control tower, surgical table, robotic arms, and user console shown in FIG. 1. The computer vision analyzer can apply one or more machine learning algorithms (e.g., neural networks) which are trained to detect and recognize (with certain probability) objects that fall into one or more classifications. Machine learning algorithm can perform classification (e.g., recognize whether an object exists in an image), object recognition (e.g., recognizing an object in a particular region), and/or semantic segmentation, (e.g., recognizing objects on a pixel level). Computer vision algorithms can include, for example, a trained deep neural network, a trained convolutional neural network, edge detection, corner detection, feature detection, blob detection, or other equivalent techniques that can be deployed to detect and recognize objects. APIs such as, for example, Tensorflow, ImageAI, or OpenCV, can be leveraged.

Through similar image processing and computer vision algorithms, the processor can, at block 50, determine position (e.g., a location in the common 3D coordinates) and orientation of the recognized objects. The robot system data can be used to determine detailed positioning of the robot arms, surgical instruments, and the surgical table. For example, the robot system data can include, among other data, an angle and height of the surgical table and joint angles of each robot arm. An object identifier such as a name or unique identifier can be associated with each of the recognized objects for reference. For example, a playback device can render a computer model of a surgical table based on identifier type and render the model in the common coordinate system based on the stored position and orientation associated with the object identifier.

In some embodiments, humans such as surgical assistants and other staff are recognized and converted to a more compressed data representation, e.g., a spline curve representation. This can further reduce footprint of the digital asset. It should be understood that a digital asset can be a digital file or a grouping of files, that are stored long-term for playback, as opposed to being stored short-term or temporarily for the purpose of processing.

To reduce data storage size and to improve later retrievability and readability, raw image data (e.g., 3D point cloud data) for unrecognized or unclassified objects in the surgical environment are stored as raw point cloud data but not for the recognized objects (which can be stored as position and orientation, or as spline data) as discussed in other sections. In some cases, the 3D point cloud data for unrecognized objects can, at block 48, be converted to mesh data, e.g., polygon mesh, triangle mesh, or as spline data. The processor can perform one or more conversion algorithms to convert the 3D point cloud data to mesh data, for example, Delaunay triangulation, alpha shapes, ball pivoting, and other equivalent techniques.

In some embodiments, unrecognized objects can be stored and further analyzed offline at block 46. Offline, in this context, means that the processes of providing real-time feedback and producing a digital asset for playback do not wait for or hinge upon this offline analysis. In this block, the unrecognized objects can be continuously analyzed offline as subsequent surgeries are performed until the unrecognized objects are classified. The point cloud data that includes unrecognized objects can be stored in computer readable memory (e.g., in a networked server) and analyzed by an automated computing platform (using computer vision algorithms) and/or by scientists and other people to recognize and classify the unrecognized objects.

The point cloud data can include timestamp data which allows the data to be temporally fused with other sensor data retrieved from the surgical robotic system, such as microphones or cameras on the surgeon bridge and robotic logs. The fused data can further help classify and recognize the objects. The new classifications can be used to train machine learning algorithms for computer vision which can then be used by the processor to "recognize" these objects in the digitization of future surgical exercises.

For example, referring to FIG. 1, some mayo stands (e.g., stand 19), a first assistant 8, chairs or shelving units 18, or lighting booms might go unrecognized in one or more earlier exercises. These objects can be classified offline and then used to recognized these or similar objects in later exercises, thereby improving the online analysis and reducing footprint of the digital asset over repetitions. As described in other sections, these objects, after becoming recognized, can be represented by position and orientation in the OR for the purpose of storage, and replaced with a computer generated model or representation during playback, as with other recognized objects. Computer based object recognition for unclassified objects can either occur in real-time in the OR, or using offline analysis in the cloud after the data has been uploaded to servers.

Additionally, or alternatively, key surgical events, which are described in other sections, can also be identified offline by the automated computing platform and/or by scientists or other persons. The computing platform can train machine learning algorithms to identify further surgical events based on position, orientation, movement of surgical staff, robot arms, UIDs, surgical instrument/tool, that are useful for post-operative analysis.

Referring back to FIG. 3, the combiner 52 can combine the various data into one or more digital assets for future playback. In some embodiments, the point cloud data of unrecognized objects, position and orientation associated with one or more recognized objects, and the robot system data is stored as a digital asset. In some embodiments, the digital asset further includes endoscope images that are captured during the surgical exercise. The data is synchronized temporally (e.g., with time stamps) so that it resembles the original surgical exercise when played back.

In some embodiments, high-resolution data (spatial resolution and/or temporal resolution) such as the raw 3D point cloud data or a high-resolution mesh data generated from the 3D point cloud data will be stored in the cloud for the service team, debugging, and data analysis. This high-resolution digital asset can be analyzed offline. However, for replaying this data on a consumer-facing device, the combiner can down sample the robot system data. Further, point cloud data or mesh data can be streamed "as-needed" so as to reduce the computational complexity for low-power consumer devices and to reduce the network traffic required to view different sections of the surgery. Examples of a low-power consumer device include a laptop, a smartphone running a mobile app, or a mobile, untethered virtual reality (VR) device that is Wi-Fi-connected.

A buffering, or staging server 26 can host digital asset which can be provided as streams of surgical data, in a consumer-facing application that allows customers to replay a surgery that has had its data fused by timestamp. This digital asset can be streamed to playback devices for example, through a communication network (e.g., TCP/IP, Wi-Fi, etc.). An example of a digital asset is shown in FIG. 4.

Figure 4:
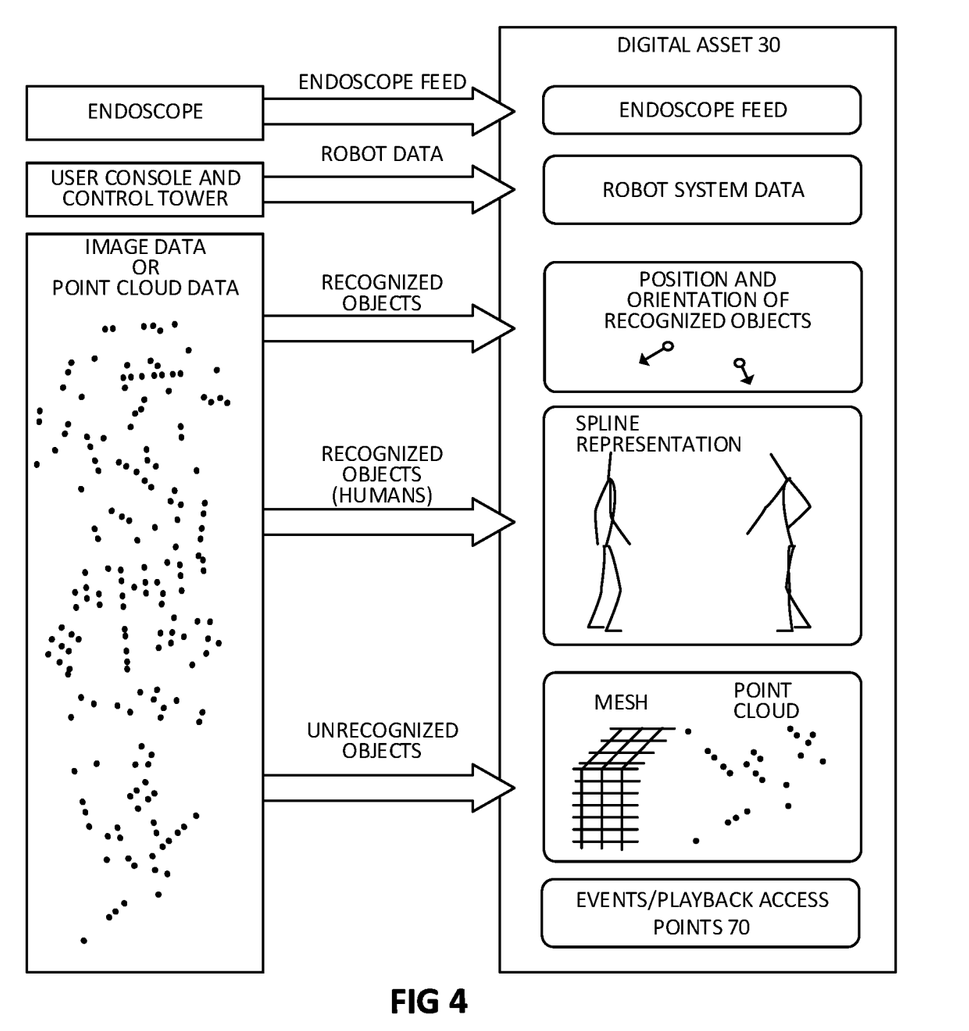
FIG. 4 shows an example of a digitized surgical exercise, according to some embodiments.

FIG. 4 illustrates a digital asset 30 as described according to some embodiments. The digital asset can include image data (e.g., 3D point cloud or mesh data) containing unrecognized objects, compressed data associated with recognized objects, logged surgical robotic data, and endoscopic feed. This data can be fused through timestamps in the separate data collections. The endoscope feed can be a stereo video feed captured by an endoscope used during the surgical exercise. The endoscopic feed can have image data capturing the inside of a patient.

The digital asset can include robot system data that is logged during the surgical exercise. The logged robot system data can include at least one of: UID state, including position, rotation, and raw electromagnetic (EM) sensor data; pedal state; instrument state, including position rotation, and energy/force applied; robot arm state, including joint values and mode; table state, including position and rotation; system errors or information, e.g., Wi-Fi connection, which surgeon is logged-in, GUI state/info, and which touchpoints are pressed/depressed on the robot.

The digital asset includes recognized objects extracted from the 3D point cloud data. The recognized objects can include components of the surgical robotic system described in FIG. 1, such as, for example, a position and orientation of the user console, surgical table and robot arms, control tower, and mobile electronic device 20 described in other sections. Further, as the system's intelligence platform advances (e.g., through offline analysis), additional objects can be recognized and stored in the digital asset. For example, mayo stands, displays, and other equipment that are not part of the surgical robotic system shown in FIG. 1 can increasingly be recognized automatically by the system and included as recognized objects. The recognized objects can include people stored as spline curve data and/or as position and orientation and joint values for leg joints, shoulders, neck, arm joints, and other human joints.

Further, the digital asset can also include 3D point cloud data or mesh data for unrecognized and unknown objects, for example, used bandages on the floor, unknown surgical instruments and equipment, and more. Thus, recognized objects can be represented in compressed form while unrecognized objects are represented with compressed data.

A playback device can render models that correspond to the recognized objects based on the position and orientation of the recognized objects. For example, a model of the surgical table and robot arms can be rendered over point cloud or mesh data that defines walls, floor, and ceiling of an OR. The model is rendered with a position and orientation specified by the digital asset in the common coordinate system. Detailed position and of the surgical table and robot arm can be memorialized in the logged robot system data and rendered based on the same.

Figure 5:
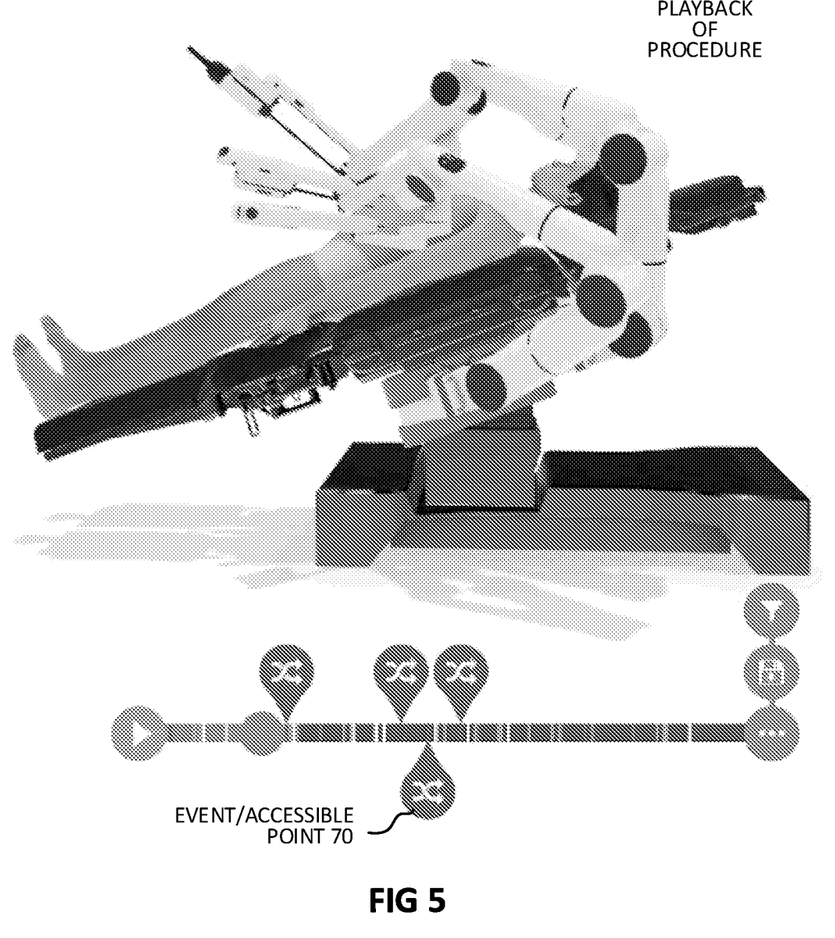
FIG. 5 shows accessible events of a digitized surgical exercise, according to some embodiments.

As described in other sections, the digital asset can include events 70 that are associated with a timeline or frames of the digital asset. The events can provide playback access points that a user can jump to during playback, for example, as shown in FIG. 5. Noteworthy events can be automatically determined based on analysis of the digitized surgical exercise. For example, the processor of FIG. 2 or FIG. 3 or an offline computing platform can analyze the surgical robotic system data such as joint values of the robot arm or movements and states of surgical instruments, position and/or movement of assistants, UID inputs, endoscope feed images, and more, to determine key events. Analysis can be performed using machine learning, decision trees, programmed logic, or any combination of such, to determine key events.

For example, robotic system data (e.g., telemetry) can be analyzed to directly indicate events such as when UIDs engaged for surgery, when a surgeon is changed, when instruments are changed. An offline platform can apply one or more machine learning algorithms (e.g., offline) to the endoscope feed, the robotic system data, and the image data, to generate events that indicate at least one of: when a trocar is inserted, a phase change, an unusually slow section of surgery, a bad patient position, robot arm collision, an incorrect OR staff position, an improper trocar position or insertion port location. Each event can be associated with a point in time or a frame of the digital asset. Thus, a user can jump straight to events of interest or search a collection of exercises to extract exercises that show particular events.

In addition to jump points, the digital asset can be sped up or slowed down. For example, users can have the option of playing through a surgery by requesting incremental data about the surgery from the staging server at a rate that exceeds the real-time playback speed of the surgery (e.g., 1.5×, 2.0×, or 3.0×).

Figure 6:
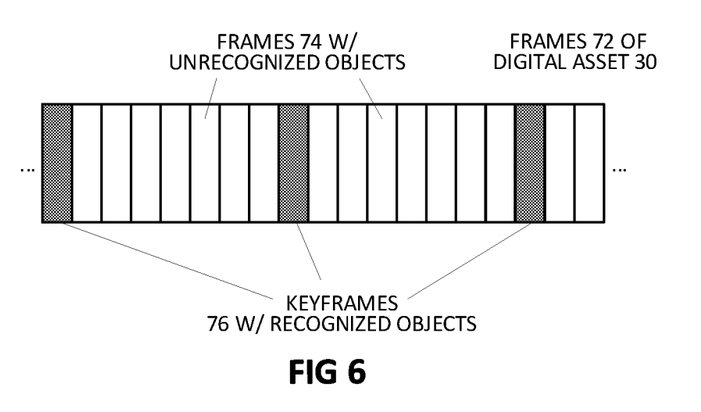
FIG. 6 shows digitized 3D data of a surgical exercise, according to some embodiments.

Referring to FIG. 6, the digital asset 30 can include a sequence of frames 72 generated based on the 3D image data captured by 3D scanners. Frames 74 can include the point cloud data or mesh data of unrecognized objects, and/or room geometry such as floors, walls and ceilings. The key frames 76 can be temporally dispersed in the sequence of frames 72 that include the position and orientation of the one or more recognized objects. Further, every key frame is not required to contain every recognized object. For example, key frames can include only those recognized objects that have values (e.g., position and orientation or spline data) that are changed from a previous key frame. This can further reduce digital asset footprint and promote computational efficiency.

Figure 7:
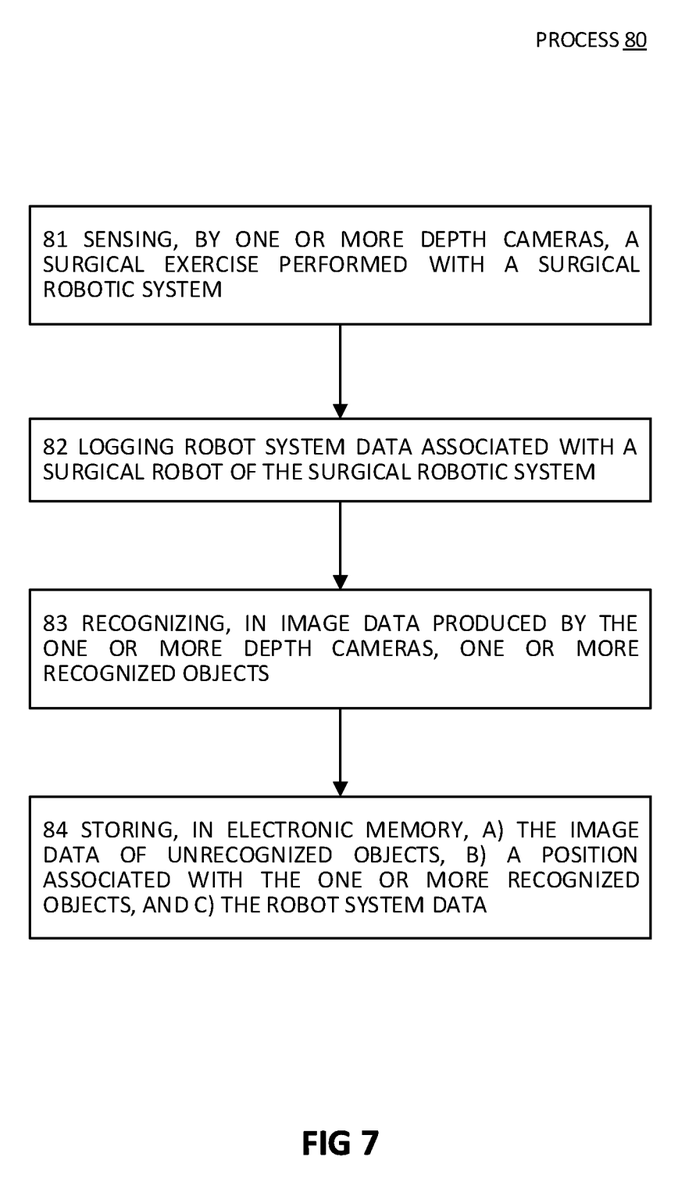
FIG. 7 shows a process for digitizing a surgical exercise, according to some embodiments.

Referring to FIG. 7, a method or process 80 is shown for digitizing a surgical exercise according to some embodiments. The method can be performed by one or more processors, for example, as shown in FIG. 2 and FIG. 3.

At operation 81, the process includes sensing, by one or more depth cameras, a surgical exercise performed with a surgical robotic system. As described, the one or more depth cameras (also known as 3D scanners) can be integrated with components of the surgical robotic system, mounted on walls or on a stand in the OR, and/or integrated with a portable electronic device (e.g., a tablet computer).

At operation 82, the process includes logging robot system data associated with a surgical robot of the surgical robotic system. This robot system data can define position (e.g., joint values) of the robot arm, surgical table height and angle, and various other telemetry data of the surgical robotic system, as described in other sections.

At operation 83, the process includes recognizing, in image data produced by the one or more depth cameras, one or more recognized objects. This can be performed using computer vision algorithms. As discussed in other sections, the recognized objects can include components of the surgical robotic system as well as other common components. The library of recognizable objects can grow over repetitions as these classifications expand to cover new objects.

At operation 64, the process includes storing, in electronic memory, a) the image data of unrecognized objects, b) a position and orientation associated with the one or more recognized objects, and c) the robot system data. The image data can be stored as 3D point cloud data, 3D mesh data, or other equivalent representation.

In some embodiments, operation 64 instead includes storing, in electronic memory, a) spline curve, mesh representation, or position, orientation, and joint values of one or more humans recognized in the image data, b) the 3D point cloud data (or mesh data) of unrecognized objects, and c) the robot system data, as a digital asset for playback of the surgical exercise. One or more events that serve as jump points that are directly accessible during the playback of the digital asset can be determined based on position or movement of the one or more humans or the robot system data or the robot system data, as described in other sections.

Taken together, embodiments of the present disclosure allow for a digital reconstruction of the operating room, which supports pre-operative planning and replay of surgeries. Awareness of where physical objects are in the scene and what people are doing at any one point in time is promoted. Post-operative analysis is also supported. Offline analysis of key events during surgery is enhanced. Explanation can be provided for the cause of different issues during surgery. Data is generated such that operating room staff can identify the problems and their causes. Intra-operative guidance is also addressed. Embodiments described can capture data outside of the endoscope and robot logs. The endoscope analysis and robotic logs can be fused with operating room analysis. OR staff can be alerted to key events (e.g., in real-time) to avoid surgical errors, increase surgical speed, improve patient outcomes, and improve the ergonomics/human factors of the surgical robotic system for its users.

In some embodiments, the various blocks and operations can be described by one or more processors executing instructions stored on a computer readable medium. Each processor may include a single processor or multiple processors with a single processor core or multiple processor cores included therein. Each processor may represent one or more general-purpose processors such as a microprocessor, a central processing unit (CPU), or the like. More particularly, each processor may be a complex instruction set computing (CISC) microprocessor, reduced instruction set computing (RISC) microprocessor, very long instruction word (VLIW) microprocessor, or processor implementing other instruction sets, or processors implementing a combination of instruction sets. Each processor may also be one or more special-purpose processors such as an application specific integrated circuit (ASIC), a cellular or baseband processor, a field programmable gate array (FPGA), a digital signal processor (DSP), a network processor, a graphics processor, a communications processor, a cryptographic processor, a co-processor, an embedded processor, or any other type of logic capable of processing instructions.

Modules, components and other features, such as algorithms or method steps described herein can be implemented by microprocessors, discrete hardware components or integrated in the functionality of hardware components such as ASICS, FPGAs, DSPs or similar devices. In addition, such features and components can be implemented as firmware or functional circuitry within hardware devices; however, such details are not germane to embodiments of the present disclosure. It will also be appreciated that network computers, handheld computers, mobile computing devices, servers, and/or other data processing systems which have fewer components or perhaps more components may also be used with embodiments of the disclosure.

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as those set forth in the claims below, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Embodiments of the disclosure also relate to an apparatus for performing the operations herein. Such a computer program is stored in a non-transitory computer readable medium. A machine-readable medium includes any mechanism for storing information in a form readable by a machine (e.g., a computer). For example, a machine-readable (e.g., computer-readable) medium includes a machine (e.g., a computer) readable storage medium (e.g., read only memory ("ROM"), random access memory ("RAM"), magnetic disk storage media, optical storage media, flash memory devices).

The processes or methods depicted in the preceding figures may be performed by processing logic that comprises hardware (e.g., circuitry, dedicated logic, etc.), software (e.g., embodied on a non-transitory computer readable medium), or a combination of both. Although the processes or methods are described above in terms of some sequential operations, it should be appreciated that some of the operations described may be performed in a different order. Moreover, some operations may be performed in parallel rather than sequentially.

Embodiments of the present disclosure are not described with reference to any particular programming language. It will be appreciated that a variety of programming languages may be used to implement the teachings of embodiments of the disclosure as described herein.

In the foregoing specification, embodiments of the disclosure have been described with reference to specific exemplary embodiments thereof. It will be evident that various modifications may be made thereto without departing from the broader spirit and scope of the disclosure as set forth in the following claims. The specification and drawings are, accordingly, to be regarded in an illustrative sense rather than a restrictive sense. The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications, and they thereby enable others skilled in the art to best utilize the invention and various embodiments with various modifications as are suited to the particular use contemplated. It is intended that the following claims and their equivalents define the scope of the invention.

What is claimed is:

1. A method performed by one or more processors during a surgical procedure, the method comprising:
receiving, from a camera arranged in an operating room, point cloud data;
recognizing an object within the operating room based on the point cloud data;
providing user feedback based on the recognized object during the surgical procedure; and
storing a portion of the point cloud data that is associated with an unrecognized object and a position associated with the recognized object within the operating room as a digital asset.

2. The method of claim 1, wherein the camera is arranged on a portable electronic device that is used in the operating room during the surgical procedure.

3. The method of claim 1 further comprising receiving endoscope images captured by an endoscope during the surgical procedure, wherein the endoscope images are stored in the digital asset along with the portion of the point cloud data and the position associated with the recognized object.

4. The method of claim 1 further comprising identifying that a surgical event has occurred during the surgical procedure based on the recognized object, wherein the feedback comprises an alert indicating that the surgical event has occurred.

5. The method of claim 4, wherein the recognized object comprises a person and the surgical event comprises the person standing at a location within the operating room, wherein the alert comprises instructions for the person to move to a new location within the operating room.

6. The method of claim 5, wherein the person is represented in the digital asset as one or more joint values or one or more spline curves.

7. The method of claim 1 further comprises logging robot system data associated with a surgical robotic system that is being used to perform the surgical procedure, wherein the feedback is based on the robot system data and the recognized object.

8. The method of claim 7, wherein the robot system data comprises at least one of: position or rotation of a user interface device that controls operation of the surgical robotic system, electromagnetic sensor data, a state of a foot pedal that controls operation of the surgical robotic system, position or rotation of a surgical instrument attached to a robot arm, force or energy applied with the surgical instrument, joint values or mode of the robot arm, network connectivity of the surgical robotic system, user log-in data, a graphical user interface state, and state of touchpoints on the surgical robotic system.

9. The method of claim 1, wherein the portion of the point cloud data and the position are synchronized temporally within the digital asset.

10. A surgical robotic system comprising:
a camera arranged in an operating room;
at least one processor; and
memory having instructions stored therein which when executed by the at least one processor causes the surgical robotic system to:
receive, during a surgical procedure performed in the operating room, point cloud data;
recognize an object within the operating room based on the point cloud data;
provide feedback based on the recognized object during the surgical procedure; and
store a portion of the point cloud data that is associated with an unrecognized object and a position associated with the recognized object within the operating room as a digital asset.

11. The surgical robotic system of claim 10, wherein the camera is arranged on a portable electronic device that is used in the operating room during the surgical procedure.

12. The surgical robotic system of claim 10 further comprising an endoscope for capturing endoscope images during the surgical procedure, wherein the endoscope images are stored in the digital asset along with the portion of the point cloud data and the position associated with the recognized object.

13. The surgical robotic system of claim 10, wherein the memory has further instructions to identify that a surgical event has occurred during the surgical procedure based on the recognized object, wherein the feedback comprises an alert indicating that the surgical event has occurred.

14. The surgical robotic system of claim 13, wherein the recognized object comprises a person and the surgical event comprises the person standing at a location within the operating room, wherein the alert comprises instructions for the person to move to a new location within the operating room.

15. The surgical robotic system of claim 14, wherein the person is represented in the digital asset as one or more joint values or one or more spline curves.

16. The surgical robotic system of claim 10, wherein the memory comprises further instructions to log robot system data associated with the surgical robotic system that is being used to perform the surgical procedure, wherein the feedback is based on the robot system data and the recognized object.

17. The surgical robotic system of claim 16, wherein the robot system data comprises at least one of: position or rotation of a user interface device that controls operation of the surgical robotic system, electromagnetic sensor data, a state of a foot pedal that controls operation of the surgical robotic system, position or rotation of a surgical instrument attached to a robot arm, force or energy applied with the surgical instrument, joint values or mode of the robot arm, network connectivity of the surgical robotic system, user log-in data, a graphical user interface state, and state of touchpoints on the surgical robotic system.

18. The surgical robotic system of claim 10, wherein the portion of the point cloud data and the position are synchronized temporally within the digital asset.

19. A non-transitory machine-readable medium comprising instructions which when executed by at least one processor:
receive, from a camera arranged in an operating room and during a surgical procedure, point cloud data;
recognize an object within the operating room based on the point cloud data;
provide feedback based on the recognized object during the surgical procedure; and
store a portion of the point cloud data that is associated with an unrecognized object and a position associated with the recognized object within the operating room as a digital asset.

20. The non-transitory machine-readable medium of claim 19 comprises further instructions to log robot system data associated with a surgical robotic system that is being used to perform the surgical procedure, wherein the feedback is based on the robot system data and the recognized object.

* * * * *

UNITED STATES PATENT AND TRADEMARK OFFICE
CERTIFICATE OF CORRECTION

PATENT NO. : 12,237,072 B2  
APPLICATION NO. : 18/449270  
DATED : February 25, 2025  
INVENTOR(S) : Olson et al.

Page 1 of 1

It is certified that error appears in the above-identified patent and that said Letters Patent is hereby corrected as shown below:

In the Claims

Column 15  
Line 14, Claim 01, delete "user"

Signed and Sealed this  
First Day of April, 2025

Coke Morgan Stewart  
*Acting Director of the United States Patent and Trademark Office*